United States Patent [19]

Horbett et al.

[11] Patent Number: 4,919,659

[45] Date of Patent: Apr. 24, 1990

[54] RADIO FREQUENCY PLASMA DEPOSITED POLYMERS THAT ENHANCE CELL GROWTH

[75] Inventors: Thomas A. Horbett; Buddy D. Ratner; Joseph A. Chinn, all of Seattle, Wash.; Yasmeen Haque, Pasadena, Calif.

[73] Assignee: The Board of Regents for the University of Washington, Seattle, Wash.

[21] Appl. No.: 136,457

[22] Filed: Dec. 21, 1987

Related U.S. Application Data

[63] Continuation of Ser. No. 809,927, Dec. 16, 1985, abandoned.

[51] Int. Cl.$^5$ .............................................. A61F 2/06
[52] U.S. Cl. .......................................... 623/1; 623/66; 429/2; 429/40; 429/41; 435/240; 435/243; 435/285
[58] Field of Search ...................... 427/2, 45.1, 40, 41; 435/284, 285, 286, 240–243; 623/1, 66

[56] References Cited

U.S. PATENT DOCUMENTS

| | | | |
|---|---|---|---|
| 3,853,712 | 12/1974 | House et al. | 435/285 |
| 3,910,819 | 10/1975 | Rembaum et al. | 435/285 |
| 3,941,661 | 3/1976 | Noteboom | 435/285 |
| 4,144,126 | 3/1979 | Burbidge | 435/240 |
| 4,224,413 | 9/1980 | Burbidge | 435/284 |
| 4,238,568 | 12/1980 | Lynn | 435/285 |
| 4,312,575 | 1/1982 | Peyman et al. | 427/41 X |
| 4,337,104 | 6/1982 | Lynn | 435/285 X |
| 4,373,027 | 2/1983 | Berneman et al. | 435/286 X |

FOREIGN PATENT DOCUMENTS

| | | | |
|---|---|---|---|
| 22691 | 2/1982 | Japan | 435/240 |
| 0079882 | 5/1982 | Japan | 435/240 |
| 146568 | 9/1982 | Japan | 435/284 |
| 2116206 | 9/1983 | United Kingdom . | |

OTHER PUBLICATIONS

Yasuda, H., *Plasma Polymerization*, Academic Press, Inc., 1985, pp. 114–131.

*Primary Examiner*—Michael Lusignan
*Attorney, Agent, or Firm*—Seed and Berry

[57] ABSTRACT

A method for enhancing bio-material capability for use as a supporting surface for cell culture is disclosed. The method requires exposure of the bio-material to a plasma polymerizable polymer gas, which includes oxygen-containing organic molecules. The material surfaces are then subjected to an RF plasma gas discharge in the presence of the gas, causing a deposition on the exposed material surfaces of a conformal overcoating of the polymer on the material. The deposition enhances fibronectin adsorption and hence cell attachment, spreading and cell growth. Preferred polymerizable gases are acetone, methanol, and ethylene oxide.

15 Claims, 12 Drawing Sheets

Acetone Plasma-Treated Polystyrene, High Res, 10 Minute Reaction

| Energy | Width | Area | % |
|---|---|---|---|
| 285.00 | 1.55 | 34232 | 48.5 |
| 286.40 | 1.55 | 18525 | 26.2 |
| 287.90 | 1.55 | 14876 | 21.1 |
| 288.80 | 1.55 | 3019 | 4.3 |

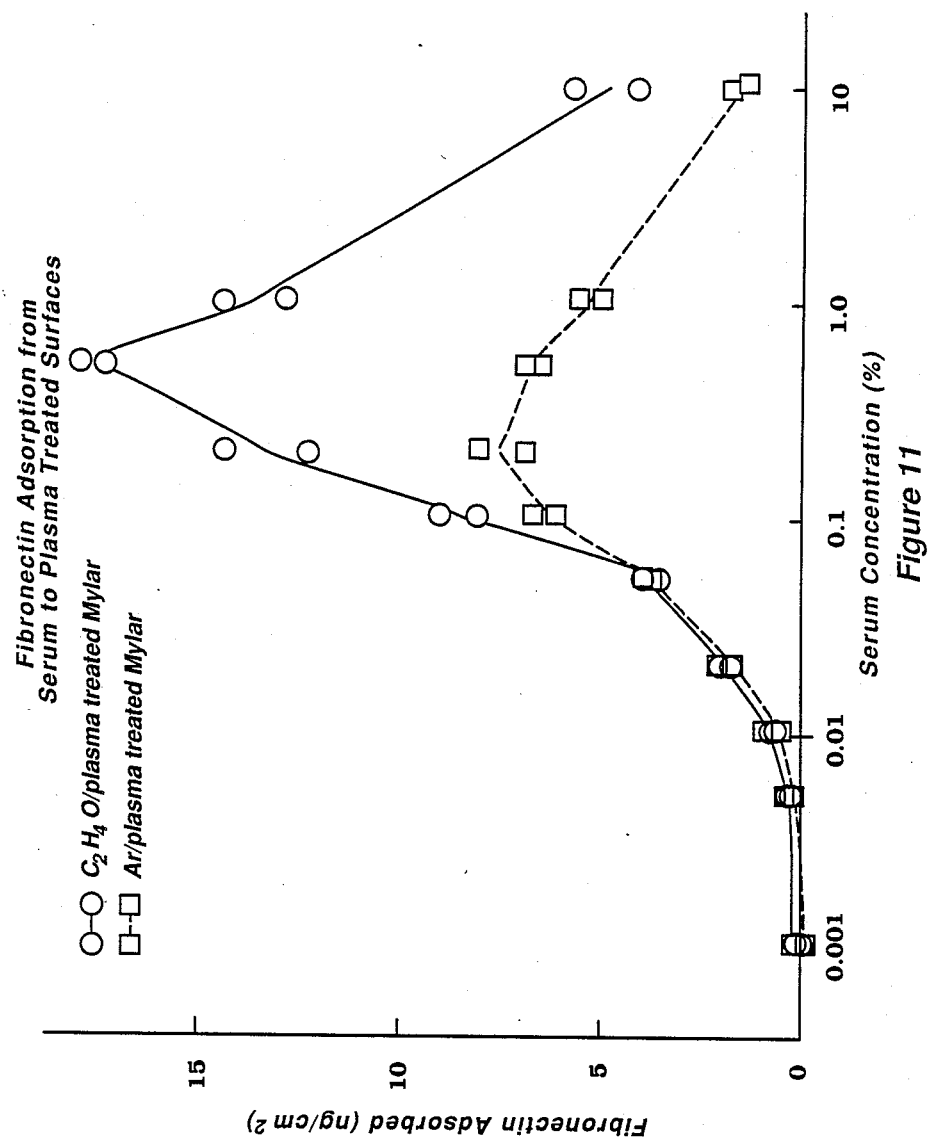

RADIO FREQUENCY PLASMA DEPOSITED POLYMERS THAT ENHANCE CELL GROWTH

This application is a continuation of U.S. patent application Ser. No. 809,927, filed Dec. 16, 1985, now abandoned under C.F.R. §1.62.

1. Technical Field

The invention is related to biocompatible materials for use as supporting surfaces for cell culture. More particularly, the invention relates to modifying bio-materials to produce surfaces which will provide support for and enhance cell culture.

2. Background Art

In cell culture, many mammalian cells require attachment to a supporting bio-compatible surface in order for the cells to grow satisfactorily. Cell spreading on the supporting material surface is also generally considered to be a prerequisite to cell division. Bio-compatible materials, often called "bio-materials," are nondegradable, nontoxic and otherwise suitable for contact with biological organisms and environments. Bio-materials differ widely in their inherent capabilities to enhance attachment, spreading and subsequent growth of cells. Selecting a suitable material to support a particular cell culture is difficult, since interactions between material surfaces and the complex protein mixtures encountered in biological environments are not well understood, and hence, not entirely predictable.

Polystyrene is an example of a commercially utilized bio-material that is fabricated into tissue culture tissues. It is generally unsuitable for vertebrate cell culture because it permits neither rapid attachment nor rapid spreading of cells. The polystyrene surface, however, may be modified to produce an excellent tissue culture supporting material. Surfaces may be improved by subjecting them to a glow discharge which etches or oxidizes the exposed polystyrene surfaces. Surfaces have been improved also by modifying them chemically. For example, surfaces exposed to sulfuric acid, chloric acid, hydrolysis and ozone analysis show improved performance as cell growth supporting materials.

Prior work on modifying surfaces for cell culture, using glow discharge or chemical means in contact with a material, renders a surface more hydrophilic, oxidizing it by attaching polar groups to the surfaces. However, the effect of these techniques only partially alters the characteristics of the bio-material. In general, sufficient of its inherent character remains exposed to significantly impact the material's performance as a cell growth support. Thus, the unsuitable aspects of a material when modified by the prior art processes are likely to continue to adversely effect cell culture.

There has been extensive interest and research in developing a better understanding of how bio-materials interact with biological systems in an effort to find or make materials which enhance cell culture. In examining bio-material interactions with cells, it is well known that bio-material surfaces exposed to biological fluids absorb proteins on their surfaces. It has been suggested that a material's suitability as a cell culture supporting surface is correlatable with its ability to bind certain proteins from biological fluids. The capability of a material to adsorb fibronectin, in particular, has been suggested as related to the surface's ability to promote cell attachment.

Other tests designed to establish the usefulness of a bio-material for cell culture include actually attaching various cell lines onto test surfaces and directly observing to the extent possible how a bio-material performs.

The reaction of polymeric surfaces to glow discharges, noted above with respect to polystyrene, has focused interest on gas plasma depositions as a means for modifying various material's surface characteristics. The gas plasma deposition method has generated a number of unique, reproducible polymer surfaces, independent of the supporting polymer intrinsic characteristics. These surfaces demonstrate pronounced, unexpected bio-interactions. Polymer surfaces have been modified by thin film deposition, using a capacitatively coupled plasma RF-discharge system, which produces surfaces having a range of surface energies which impact behavior of the materials in bio-systems. For example, vascular grafts of polymeric materials have been produced having treated surfaces rendered both thrombi- and emboli-resistant by exposing the material to a plasma gas discharge in the presence of a fluorinated hydrocarbon gas. The products produced are characterized as having low energy surfaces, including critical surface tension values lower than those for Teflon ®. The polymeric substrate produced is especially useful in contact with blood, since its being thrombi- and emboli-resistance continues for extended time periods.

Polymer surfaces have also been modified by RF plasma discharges to produce higher energy surfaces. For example, exposing a substrate to an ethylene oxide atmosphere during the plasma gas discharge produces critical surface tensions on the order of 45 dynes/cm or greater. The addition of oxygen to the plasma permits production of films with still higher critical surface tension values. The usefulness of these materials for enhancing cell culture, as supporting materials, has not, heretofore, been recognized.

DISCLOSURE OF INVENTION

It is an object of the invention to modify surfaces of bio-materials wherein the modified surfaces have an enhanced ability to adsorb a protein layer when exposed to a biological fluid. This enhanced ability of protein layer adsorption is related to an ability of the surfaces to enhance cell attachment, mass cell culture, cell growth and mass tissue culture on the modified material surface.

The method requires exposing the surface of the bio-material to a gas that is plasma polymerizable and includes oxygen-containing organic molecules. The bio-material surfaces intended for cell contact are then subjected, in the presence of the gas, to a plasma gas discharge which deposits the polymerizable gas species onto the exposed surfaces.

The suitability of a finished material is characterized by its enhanced ability to adsorb fibronectin from biological fluids. The plasma polymerizable gas is typically acetone, methanol, ethylene oxide, glutaraldehyde or mixtures thereof.

The bio-material selected for the treatment of the invention may be any material which is useful in contact with biological fluids and cell growth. The material may be a polymer, a ceramic, glass or a metal. A polymer is a preferred material and may include polyethylene, polyesters, polyacrylics, polyurethanes, polystyrene or silicon-containing polymers.

The gas plasma deposition is generated by radio frequency or microwave frequency means.

The modified surfaces are characterized as polar in nature and include oxygen containing groups pendent from said surface. The deposited polymer comprises a conformal, polymeric overcoating on the base supporting material.

The process of the invention is useful in producing articles for biological implants, in addition to supporting and enhancing cell culture. In such a case, the biomaterial may be selected from a group consisting of polyester, tetrafluoroethylene or polyurethane, in a porous form. The article surfaces which are to be exposed to biological fluids upon implantation are exposed to a plasma polymerizable gas such as acetone, methanol, ethylene oxide, glutaraldehyde or mixtures thereof, and simultaneously with the gas exposure, to an RF discharge which results in a plasma deposition on the implant surfaces. The plasma gas deposition produces an implant having overcoated surfaces which promote endothelial cell growth and heparin binding.

BRIEF DESCRIPTION OF THE DRAWINGS

FIG. 11 compares fibronectin adsorption from serum for ethylene oxide and argon-treated Mylar ®.

BEST MODE FOR CARRYING OUT THE INVENTION

Figure 1:
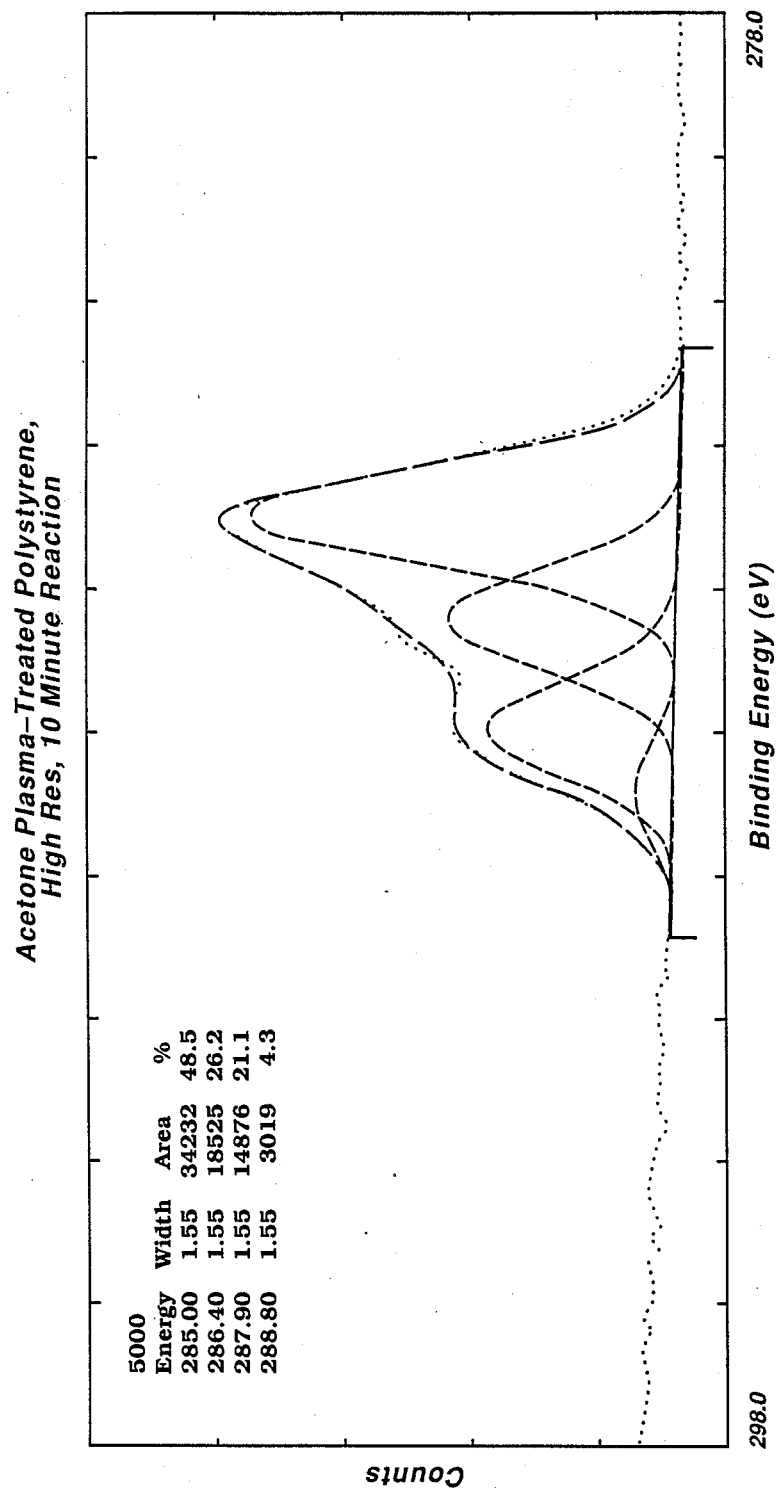
FIG. 1 is an ESCA spectrum showing surface character of an acetone plasma-treated polystyrene substrate.

In essence, the method of the invention utilizes a RF plasma deposition of a plasma polymerizable polymer onto a supporting material to enhance the material surface's ability to support tissue culture, cell growth and the like. The process deposits a thin polymeric layer onto the material, producing a conformal overcoat on the exposed surfaces of the material. Surfaces so modified by the process of the invention can be expected to perform in a predictable manner, having characteristics determined by the nature of the polymeric deposition rather than the submerged supporting material.

The preferred method of enhancing the cell culture capabilities of a material first requires exposing a polymer substrate to a plasma polymerizable gas which includes oxygen-containing organic molecules. The material and gas are then subjected to a radio-frequency (RF) electrical discharge which causes a deposition of the oxygen-containing polymer onto the material surface. By "deposition" is meant the formation of a covalent bond between the material surface and pendent groups of the polymerizing gas, which bond attaches the polymerized polymeric layer to the material surface. The material surface is completely overcoated with the deposited polymer.

The RF plasma-generating apparatus used is conventional. Modifying organic substrates by means of plasma polymerization has long been known. The process requires sealing the material or article to be modified in a glass reactor which is then evacuated. The reactor is subsequently filled with a reaction gas or mixture of gases which at least contacts the surfaces which will ultimately be in contact with cell cultures. Capacitor rings wrapped around the reaction chamber and connected to a radio frequency generator are energized to create a plasma discharge. Gas molecules present in the vapor space are bombarded by electrons having high enough energy to rupture carbon-hydrogen bonds, leading to the formation of free radicals and other chemical species. The chemical species then attach to the exposed material surfaces.

The thicknesses of the deposition can be controlled by controlling the concentration of the gas and the time for which the material surface is exposed to the plasma gas discharge. Other parameters, such as RF energy and the like, also impact the finished product character. The deposited layer is typically less than 100 Å in thickness.

The gases employed are any that are plasma polymerizable and include oxygen-containing organic molecules. Successfully modified materials are produced using, for example, acetone, ethylene oxide, methanol, glutaraldehyde, water, or mixtures of the gases.

The bio-materials from which the cell culture supportable surfaces and articles of this invention may be made include a wide range of materials. The preferred material is a polymer having characteristics suitable for a particular application but perhaps not entirely satisfactory for contact with the particular biological environment of interest. Such a polymer is, by application of the method of the invention, now suitable, since it is the character of the polymeric deposits that determines the usefulness of the material rather than the overcoated base material. Suitable polymer materials include polyethylene, polystyrene, polyesters, polyurethanes, acrylics and silicon-containing polymers. The materials may be rigid or flexible, woven or non-woven. The articles may be porous or non-porous, molded or shaped into any desired form, depending only upon the end use of the article.

Other useful materials include ceramics, glasses, and metals. Thus, the base material for supporting a cell culture may be any material that meets the requirements of the biological environment, generally independent of the material's reaction with the particular cells of interest.

A series of modified materials were produced by means of the process of the invention. The following example describes operating parameters for overcoating polystyrene with various gases.

EXAMPLE

Sample Preparation

The following plastic samples were prepared by the method of the invention or used as examples representing prior art culture materials: (1) Falcon ® bacteriological grade plastic (untreated polystyrene), (2) Falcon ® tissue culture grade plastic (polystyrene), (3) Falcon ® Primaria ™ primary tissue culture grade plastic (polystyrene), and (4) polystyrene, plasma-treated by one of the following: acetone, air, ethylene oxide or water.

Polystyrene sample disks 11.8 mm in diameter and 1 mm thick were cut from plastic tissue culture dishes using a contact lens cutting tool mounted in a drill press. Untreated polystyrene samples were cut from tissue culture dish lids, and tissue culture grade samples were cut from the dishes themselves (Falcon®, catalog no. 3303, Becton Dickinson and Company, Oxnard, CA). Primary tissue culture grade polystyrene samples were cut from primary tissue culture dishes (Falcon® Primaria ™, catalog no. 3802, Becton Dickinson and Company). Cut polystyrene samples were cleaned in a 1% soap solution in an ultrasonic cleaner for 5 minutes, followed three times by ultrasonic cleaning in purified, deionized water for 5 minutes.

Surface Modification by RF Plasma Deposition

Radio-frequency plasma polymer deposition of acetone (spectral grade), filtered air, ethylene oxide (Matheson® Gas Products, Newark, CA), methanol (spectral grade), and purified water vapor on untreated polystyrene were performed as follows. Materials to be treated were inserted into a glass vessel 75 cm in length and 10 cm in diameter, which was then sealed. The vessel was evacuated by a mechanical pump, then backfilled with the appropriate gas to be used. The system pressure was monitored by a capacitance monometer connected to an adaptive pressure control system (AdapTorr ™, power supply model AC-2, controller model ACR-26, Vacuum General). Pressure was controlled by altering the position of an in-line adjustable butterfly valve. Brass capacitor rings were wrapped around the reactor and spaced 12 inches apart. Samples to be treated were placed anywhere in a 10-inch zone centered between the rings. A 13.56 MHz RF generator (Tegal Corporation, Novato, CA) was then turned on and a plasma formed. Untreated polystyrene samples, either as received culture dishes or cut disks, were etched with an argon plasma (350 mtorr argon, 50 watts (w), 5 minutes), then exposed to a treatment gas plasma for 10 minutes (acetone: 100 mtorr, 40 w; air: 125 mtorr, 30 w; ethylene oxide: 70 mtorr, 30 w; methanol: 100 mtorr, 30 w; water: 100 mtorr, 50 w) in the plasma reactor. Vapor was continuously passed over the samples for one-half hour after the plasma reaction was terminated to quench any active surface groups. First argon, then air was bled into the reactor until the system had returned to atmospheric pressure. The reactor was then opened under a laminar flow hood and the samples were removed.

Control surfaces were prepared to facilitate the interpolation of results. In addition to the commercially available cell culture materials noted above, an untreated polystyrene substrate was coated with gelatin for comparative purposes. In addition, both ethylene oxide and acetone plasmas were used to modify a polytetrafluoroethylene (PTFE) surface (catalog no. p065005, Chemplast, Inc., Wayne, NJ), which contains repeating $CF_2$ groups.

Resulting polymeric surfaces were then analyzed by the electron spectroscopy for chemical analysis (ESCA) technique, which has a sampling depth of about 100 Å. Low resolution ESCA spectra, obtained over 20 eV ranges around the carbon, nitrogen and oxygen peaks, were utilized to determine the elemental surface compositions of various test polystyrene materials exposed to various plasma gases. Table I below reports elemental compositions for control surfaces and test surfaces of the invention. The plasma-treated surfaces differ in oxygen content, with the acetone plasma generating the greatest level.

TABLE I

ELEMENTAL ANALYSIS OF DEPOSITED POLYMER SURFACES

| Surface | Elemental Composition, % | | |
|---|---|---|---|
| | C | O | N |
| Control Surfaces | | | |
| virgin polystyrene control | 100 | 0 | 0 |
| tissue-culture grade polystyrene | 83 | 16 | 0 |
| Primaria ™ tissue-culture grade polystyrene | 68 | 15 | 17 |
| Test Surfaces | | | |
| acetic acid plasma-modified polystyrene | 76 | 18 | 6 |
| acetone plasma-modified polystyrene | 69 | 28 | 3 |
| air plasma-modified polystyrene | 64 | 33 | 3 |
| ethylene oxide plasma-modified polystyrene | 84 | 14 | 1 |
| methanol plasma-modified polystyrene | 76 | 22 | 2 |
| water plasma-modified polystyrene | 65 | 31 | 4 |

Surface compositions of test materials, as determined by high resolution ESCA spectra, are seen to depend upon the plasma surface treatment, as shown in Table II. Functional surface groups were tentatively identified by resolving the ESCA Cls spectra using least squares curve fitting methods. Plasma-deposited polymers are typically randomly functionalized, highly branched and irregularly cross-linked, making predictions of peak shifts difficult.

TABLE II

IDENTIFICATION OF SURFACE CHEMICAL GROUPS BY HIGH RESOLUTION ESCA ANALYSIS OF UNTREATED AND PLASMA-TREATED POLYSTYRENE SURFACES

| Surface | Chemical Group | | | |
|---|---|---|---|---|
| | C—H, C—C, C—C | C—O | C=O | O—C=O |
| | Binding Energy (Percent of Cls spectrum) | | | |
| untreated polystyrene control | 285.0 (100) | — | 13 — | — — |
| tissue culture grade polystyrene | 285.0 (78.4) | 285.5 (11.7) | 287.7 (5.0) | (4.8) |
| Primaria ™ tissue culture polystyrene | 285.0 (71.4) | 286.4 (10.3) | 287.5 (08.0) | (10.3) |
| gelatin coated polystyrene | 285.0 (37.7) | 286.4 (37.0) | 288.1 (25.3) | — |
| acetone plasma-treated polystyrene | 285.0 (52.4) | 286.5 (25.5) | 288.1 (22.2) | — |
| air plasma-treated polystyrene | 285.0 (75.4) | 286.5 (8.7) | 288.0 (9.2) | 289.7 (6.7) |
| ethylene oxide plasma-treated polystyrene | 285.0 (81.0) | 286.4 (11.9) | 288.0 (5.9) | 289.2 (1.2) |
| methanol plasma-treated polystyrene | 285.0 (78.6) | 286.6 (14.8) | 288.2 (6.6) | (5.0) |
| water plasma-treated polystyrene | 285.0 (80.5) | 286.4 (8.8) | 287.8 (5.4) | 289.0 (5.3) |

Figure 2:
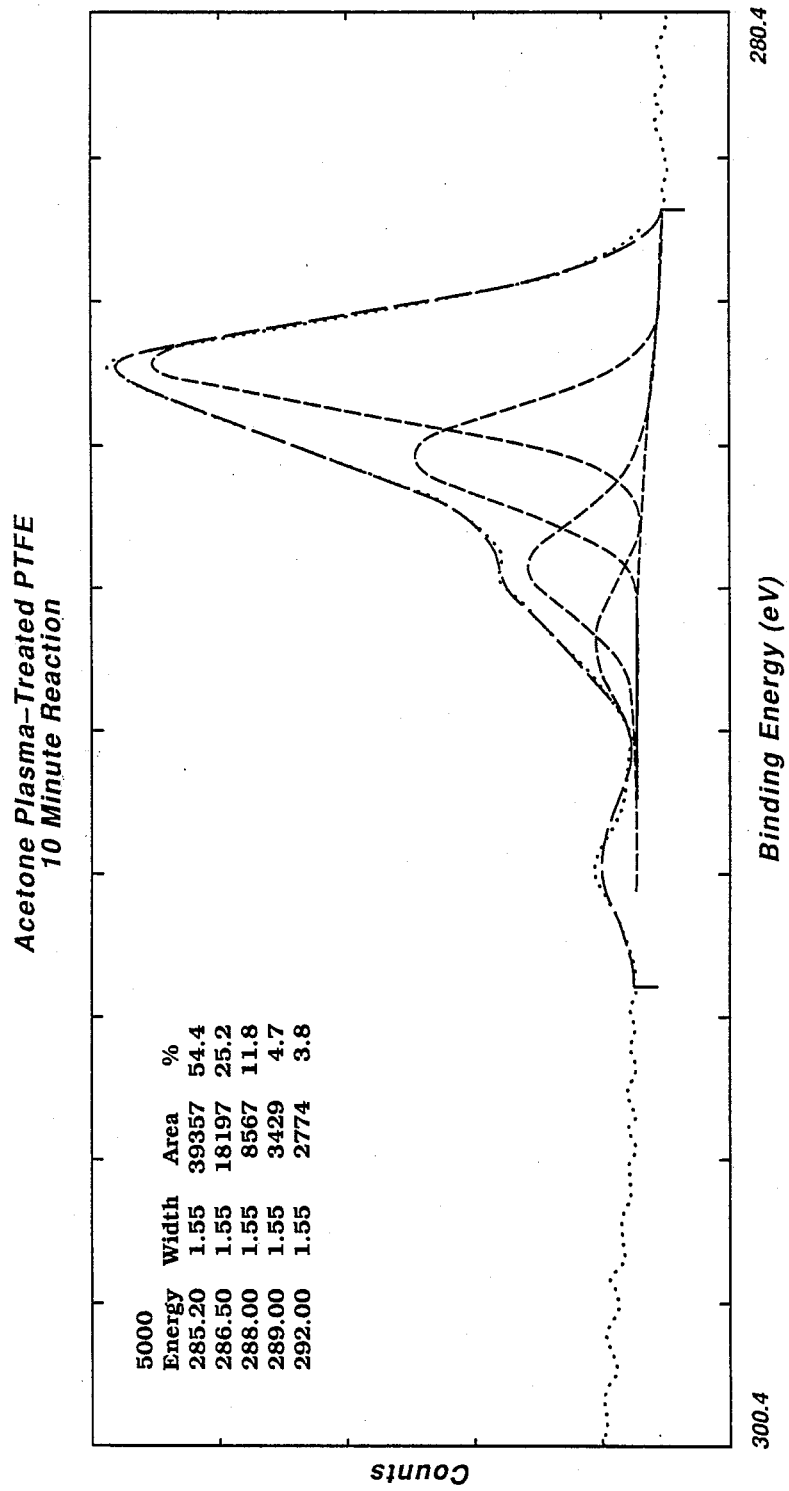
FIG. 2 is an ESCA spectrum of the surface of an acetone plasma-treated polytetrafluoroethylene substrate.

FIG. 1 shows a treated surface of the invention wherein a polystyrene substrate was exposed to an acetone plasma and RF discharge for 10 minutes as described in the example above. Separate experiments with RF plasma-deposited ethylene oxide and acetone on a Teflon ® substrate were done in order to establish correct peak assignments for the deposited films. FIG. 2 shows a treated surface of the invention from such a test. The energy of the unknown peaks in the deposits was referenced to the known binding energy for the —CF$_2$—group in the substrate.

The polar oxygen-containing groups, e.g., carboxyl, carbonyl and ester, etc., were determined to be present on the polymer material surfaces following the plasma treatment. The untreated surface exhibited a characteristic styrene pendent group peak, resulting from its aromatic structure. The disappearance of the polystyrene aromatic peak in the Cls spectra after treatment suggests that the original polystyrene substrate surface is overcoated with a new film generated in the plasma environment.

FIGS. 1 and 2 show spectra resulting from the same gas treatment on different materials. The identical high resolution spectra suggest that plasma polymerization produces surfaces independent in character of the base material.

Figure 3:
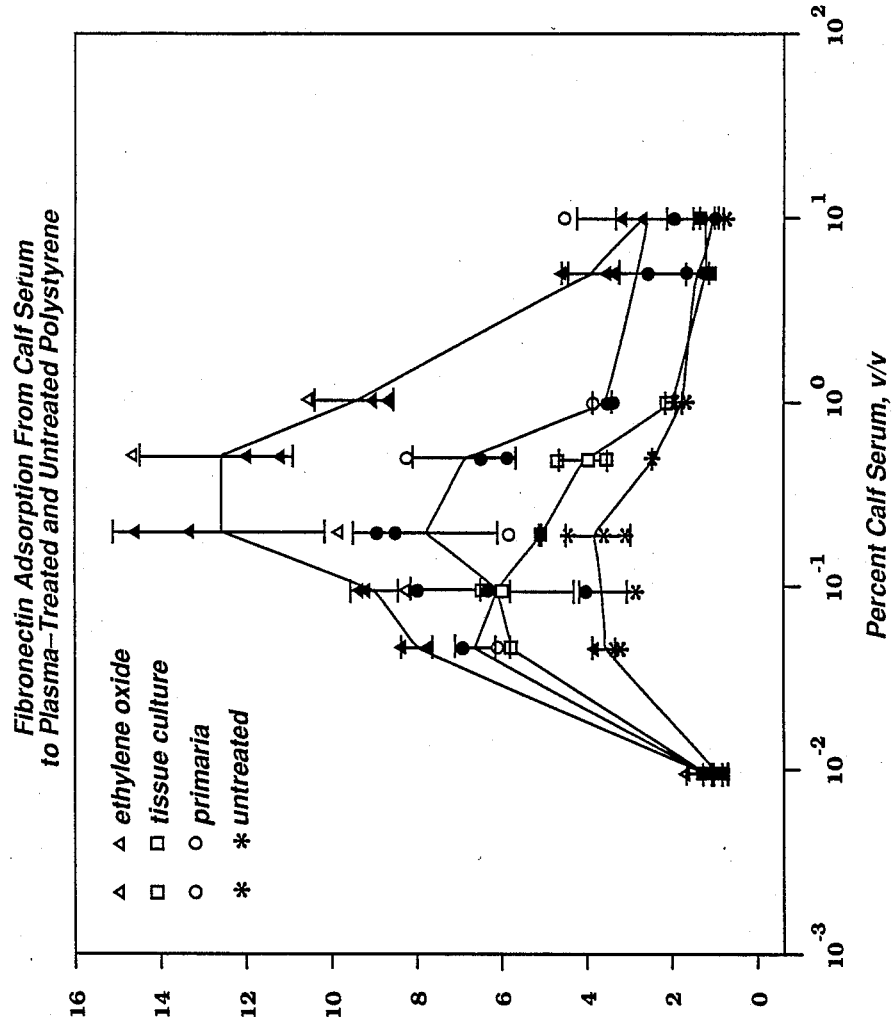
FIG. 3 shows fibronectin adsorption from calf serum for plasma-treated polystyrene.

To determine the effectiveness of the plasma gas treatment with respect to suitability of materials for cell culture, the materials were contacted with various protein-containing serums and the adsorption of fibronectin was determined. Fibronectin adsorption on plasma-treated and untreated polystyrene materials were compared. Referring to FIG. 3, experiments established that fibronectin adsorption was maximized at about the same intermediate serum concentration on ethylene oxide RF plasma-deposited surfaces. In comparison with three non-treated commercial surfaces, the ethylene oxide-treated surface adsorbed more fibronectin. As noted above, prior researchers have found that fibronectin adsorption correlates well with short term cell attachment and spreading. A material with a high affinity for fibronectin is likely a good cell culture supporting material.

Materials were tested to directly determine their interaction with cells. In a series of tests, the degree of spreading of Swiss mouse 3T3 cells on the material surfaces was determined microscopically. Spread cells had visible nuclei when observed under an inverted phase-contrast microscope. Clonal growth assays of cells on the surfaces were also performed. Cells were sparsely plated onto test surfaces, incubated for up to five days, and fixed colony size and plating efficiency were determined by examining the cells under bright field illumination of a dissecting microscope.

Figure 4A:
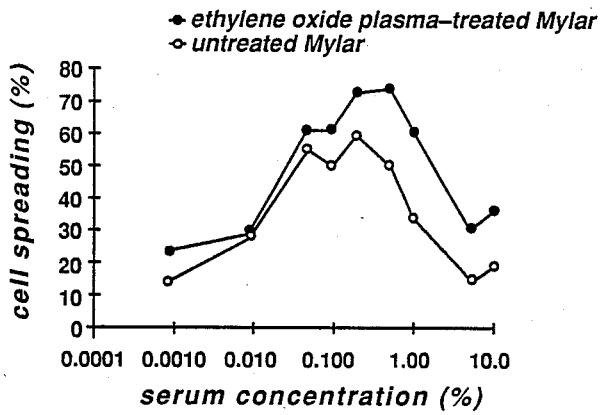
FIG. 4(a)-(c) presents 3T3 cell spreading data for ethylene oxide plasma-treated Mylar ® and polystyrene.
Figure 4B:
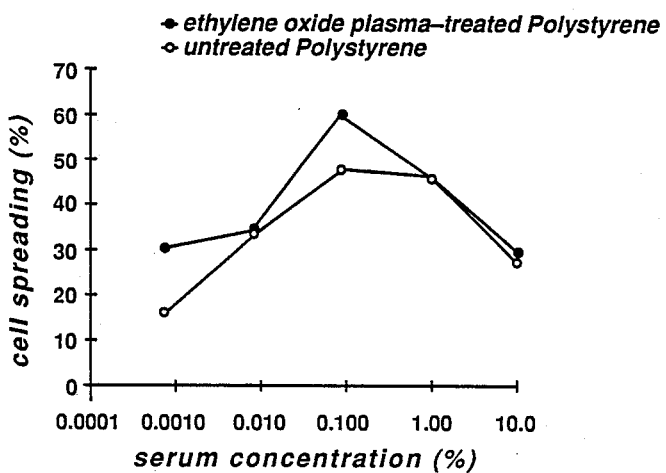
Figure 4C:
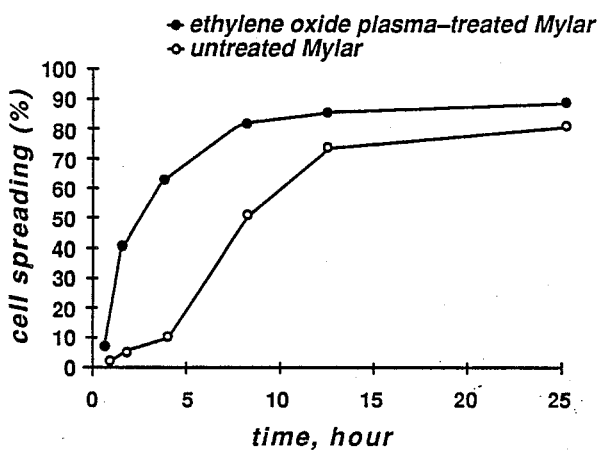

Referring to FIG. 4, the spreading of 3T3 cells after two hours of contact with ethylene oxide-treated Mylar ® (FIG. 4a) or with ethylene oxide-treated polystyrene (FIG. 4b) was higher than for untreated materials. The initial rate of spreading was much higher on ethylene-treated Mylar ®, as shown in FIG. 4c.

Figure 5:
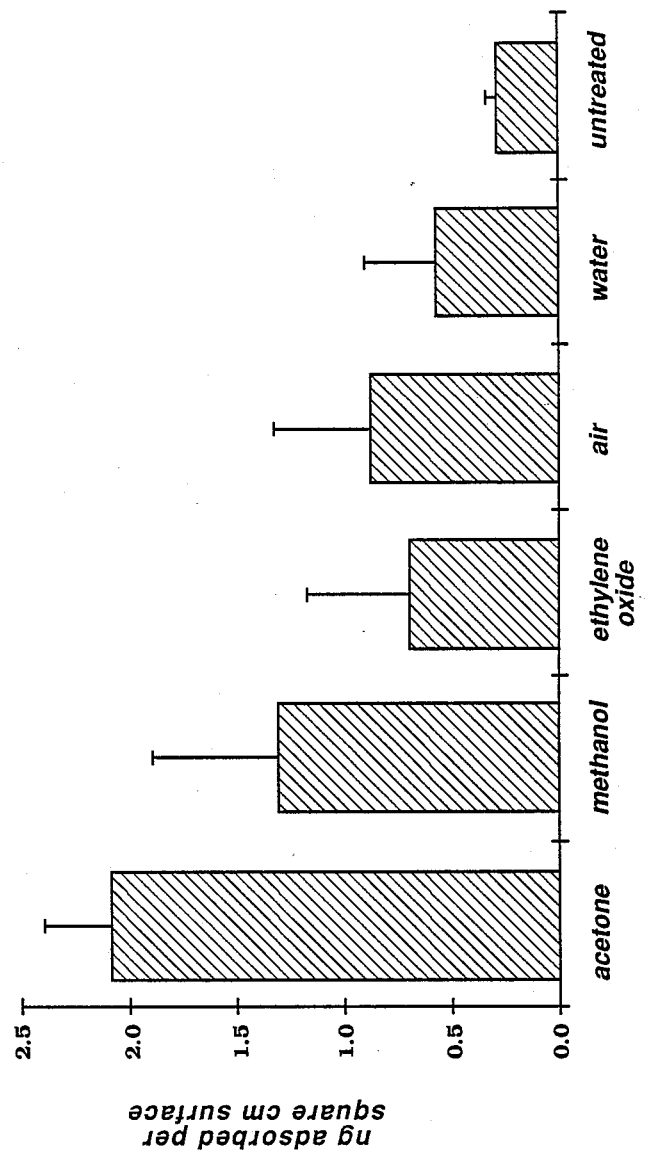
FIG. 5 is a plot of fibronectin adsorption for polystyrene treated with various gas plasmas.

The series of RF-plasma-treated polystyrene surfaces, treated by the method of the invention described in the example above, were evaluated for protein adsorption. Fibronectin adsorption, as shown in FIG. 5, varied markedly among the series. Adsorption was greatly enhanced, by a factor of 7, at 10% serum on the RF-plasma acetone-treated polystyrene in comparison with untreated polystyrene.

Figure 6:
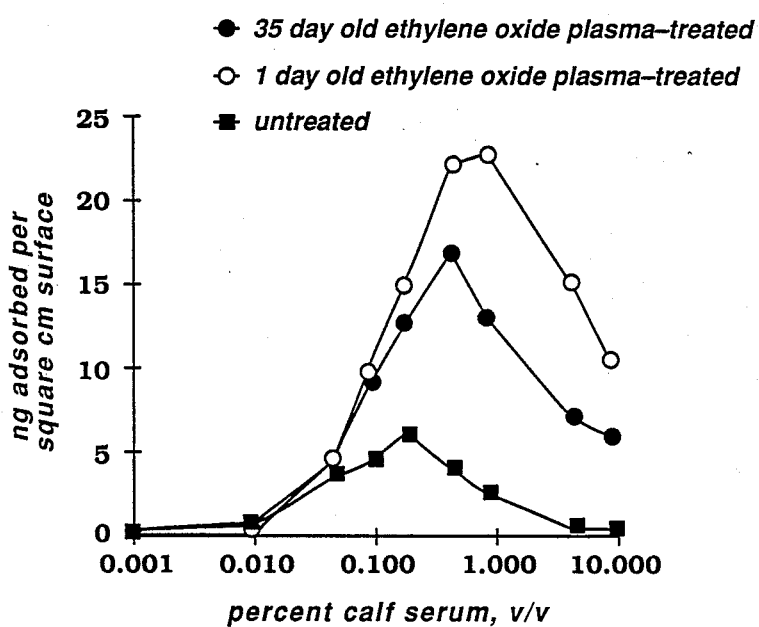
FIG. 6 shows fibronectin adsorption as a function of serum concentration for ethylene oxide plasma-treated Mylar ®.
Figure 7:
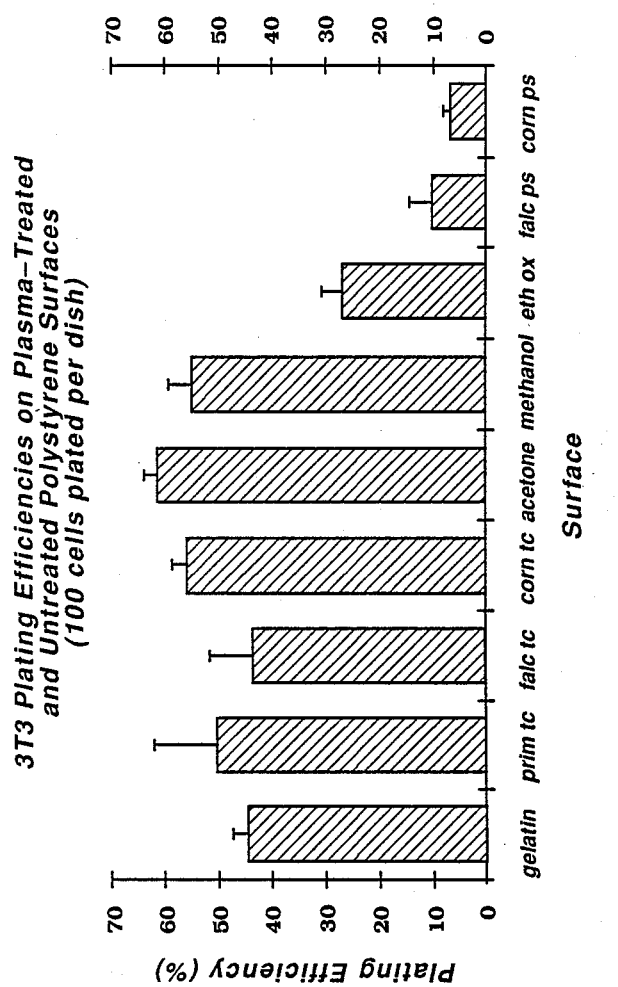
FIG. 7 is a bar graph showing 3T3 plating efficiency for plasma-treated polystyrene.
Figure 8:
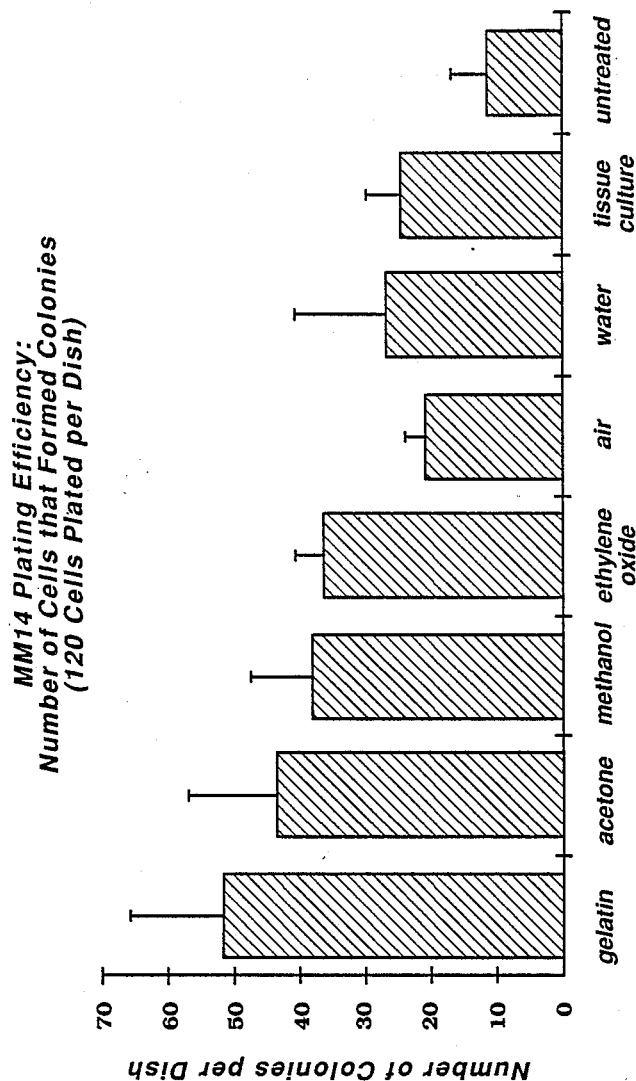
FIG. 8 shows MM14 myoblast plating efficiency for the surfaces of FIG. 7.
Figure 9:
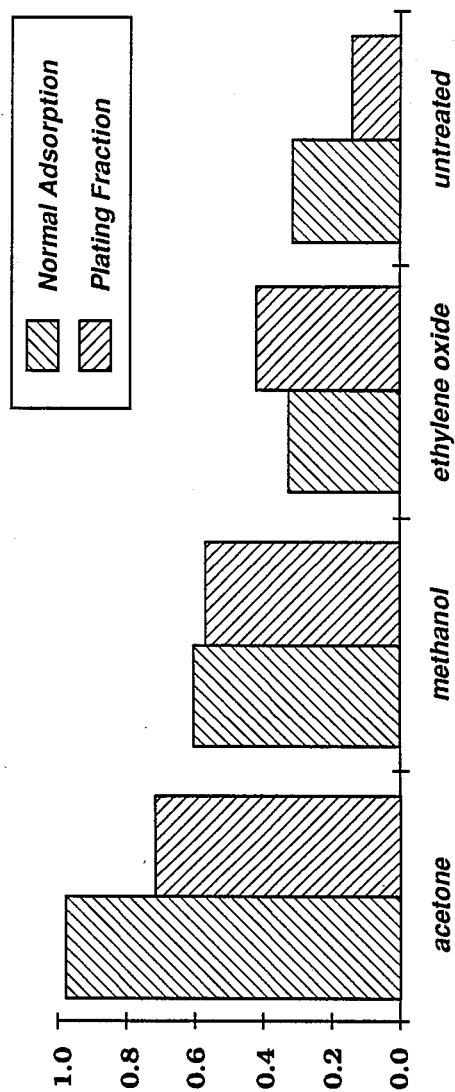
FIG. 9 correlates adsorption and 3T3 cell plating efficiency for plasma-treated polystyrene.

The adsorption data in FIG. 5 were obtained using surfaces that were treated two months prior to their use, whereas the adsorption data in FIG. 3 were obtained on freshly obtained surfaces. Adsorption of fibronectin to ethylene oxide-treated surfaces is less on the stored sample then on fresh. In a subsequent experiment, the results of which are shown in FIG. 6, evidence that aging may affect surface performance, possibly due to surface reaction or carbon contamination, was produced.

Figure 10:
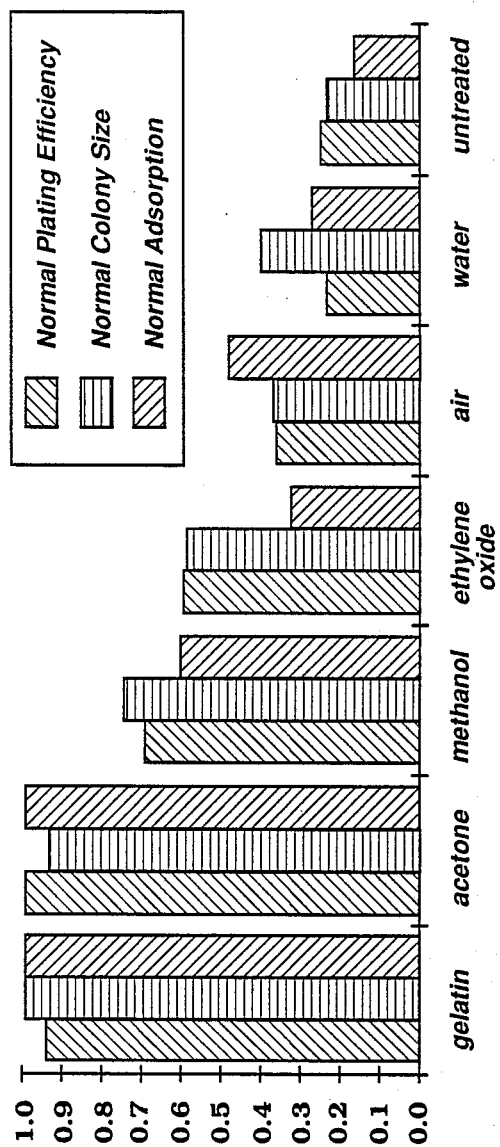
FIG. 10 correlates adsorption with myoblast behavior.

To determine if fibronectin adsorption was related to clonal growth, a series of studies were conducted. As shown in FIGS. 7-10, the plating efficiency of 3T3 fibroblasts and MM14 mouse skeletal myoblasts was determined to be higher on surfaces with higher fibronectin adsorption. With both cell lines, the acetone plasma-treated surface performed the best. As shown in FIG. 10, in the case of mouse myoblasts, the acetone plasma-modified surface performed as well as the collagen gel-coated dish.

The results of the experiments with RF plasma-modified polymer surfaces demonstrate that radio-frequency plasma polymer deposition produces enhanced cell culture materials. Although polystyrene was used as the supporting material in the majority of these experiments, the use of Mylar ®, as shown in FIG. 11, was also successful. Glass materials were also successfully modified by the method of the invention. The use of other materials is equally within the scope of the invention since the cell culture enhancement is independent of the base material. It is contemplated that surfaces may be optimized for different cell types by altering the plasma treatment and reaction conditions, such as RF power, reaction gas, and reaction time.

The products and process of the invention rely on the hypothesis that initial cellular events important in the response of a biological system to a bio-material are most likely determined by organization of a layer of adsorbed protein on the material surfaces. The organization of this layer is dictated jointly by the surface properties of the material, as well as the nature of the protein mixture surrounding the material. In the present invention, improved fibronectin adsorption on certain RF plasma-treated surfaces strongly suggests that their use in biological implants will result in improved healing. Polymer surfaces in contact with biological fluids preferentially bind fibronectin. Fibronectin is not blood compatible but fibronectin strongly binds heparin. A surface that is exposed to biological fluids containing fibronectin and heparin will be blood compatible. Such preparation of the new RF plasma-deposited surfaces will enhance endothelial cell growth on, for example, vascular grafts. Thus, the method of the invention and products produced therefrom include use as implants in biological environments.

We claim:

1. A method of depositing a polymeric overcoat layer on a bio-material wherein said deposited layer has an effective amount of oxygen-containing groups and an enhanced ability to absorb a protein layer on said deposited layer when exposed to a biological fluid, and wherein cell attachment, mass cell culture, cell growth or mass tissue culture on said deposited layer is enhanced, said method comprising:
   exposing a surface of said bio-material to an effective amount of a gas, said gas being plasma polymerizable and includes oxygen-containing organic molecules; and
   subjecting said surface, in the presence of said gas, to a plasma gas discharge wherein said enhanced protein-adsorbing surface layer is generated and attached to said exposed surface.

2. The method of claim 1 wherein said adsorbed protein layer is rich in fibronectin.

3. The method of claim 1 wherein said gas is selected from the group consisting of acetone, methanol, ethylene oxide, glutaraldehyde and mixtures thereof.

4. The method of claim 1 wherein said surface, after having been subjected to said plasma gas discharge, is further treated by exposing said surface to a biological fluid wherein a protein layer that enhances cell attachment, mass cell culture, cell growth and mass tissue culture is adsorbed by said surface.

5. The method of claim 4 wherein said protein is fibronectin and said biological fluid includes heparin.

6. The method of claim 1 wherein said material is selected from the group consisting of polymers, ceramics, glasses and metals.

7. The method of claim 6 wherein said polymer is selected from the group consisting of polyethylene, polyesters, polyacrylics, polyurethane, polystyrene, and silicon-containing polymers.

8. The method of claim 1 wherein said plasma gas deposition is generated by radio-frequency means.

9. The method of claim 1 wherein said plasma gas deposition is generated by microwave frequency means.

10. The method of claim 1 wherein said modified material surface characteristics result from said plasma-deposited polymer forming a conformal, polymeric overcoating on said material, said modified surfaces further characterized as being polar in nature and including oxygen-containing groups pendent upon said surface.

11. A biological implant article that promotes endothelial cell growth and heparin binding, said article consisting essentially of:
a porous polymer material selected from the group consisting of polyester, tetrafluoroethylene and polyurethane; and
an overcoated surface layer covalently bound to said porous polymer material and comprising a plasma gas discharge layer of gas polymer selected from the group consisting of acetone, methanol, ethylene oxide, gluteraldehyde and mixtures thereof.

12. A composite support member for cell culture comprising a body of bio-material and a plasma-polymerized surface deposit layer thereon, said surface deposit layer consisting essentially of a plasma-polymerized deposit layer from and effective amount of a plasma-polymerizable organic gas, wherein said gas includes oxygen-containing organic molecules, and covalently bonded to the surface of said bio-material through pendent oxygen-containing groups of the plasma-polymerizable gas.

13. A support member according to claim 12 wherein said bio-material is selected from the group consisting of polymers, ceramics, glasses, and metals.

14. A support member according to claim 13 wherein said polymer is selected from the group consisting if polyethylenes, polyesters, polyacrylics, polyurethanes, polystyrenes, and silicon-containing polymers.

15. A support member according to claim 12 wherein said gas is selected from the group consisting of acetone, methanol, ethylene oxide, glutaraldehyde, and mixtures thereof.

* * * * *

UNITED STATES PATENT AND TRADEMARK OFFICE
CERTIFICATE OF CORRECTION

PATENT NO. : 4,919,659
DATED : April 24, 1990
INVENTOR(S) : Thomas A. Horbett, et. al.

It is certified that error appears in the above-indentified patent and that said Letters Patent is hereby corrected as shown below:

Column 1, after the Title, insert before the cross-reference, --This invention was made with government support under grant number HL 19419 awarded by the National Institutes of Health. The government has certain rights in the invention--.

Signed and Sealed this

Twenty-eighth Day of September, 1993

Attest:

BRUCE LEHMAN

Attesting Officer

Commissioner of Patents and Trademarks